United States Patent
Ding

(10) Patent No.: US 10,359,345 B2
(45) Date of Patent: Jul. 23, 2019

(54) METHOD FOR PREPARING LIQUID-STATE DRIPPING OR COATING PATHOLOGICAL QUALITY CONTROL PRODUCT AND USES THEREOF

(71) Applicant: Wei Ding, Hangzhou (CN)

(72) Inventor: Wei Ding, Hangzhou (CN)

( * ) Notice: Subject to any disclaimer, the term of this patent is extended or adjusted under 35 U.S.C. 154(b) by 0 days.

(21) Appl. No.: 15/511,575

(22) PCT Filed: Apr. 23, 2015

(86) PCT No.: PCT/CN2015/077297
§ 371 (c)(1),
(2) Date: Mar. 15, 2017

(87) PCT Pub. No.: WO2016/123868
PCT Pub. Date: Aug. 11, 2016

(65) Prior Publication Data
US 2017/0284909 A1    Oct. 5, 2017

(30) Foreign Application Priority Data

Feb. 6, 2015   (CN) .......................... 2015 1 0062783

(51) Int. Cl.
| | |
|---|---|
| *G01N 1/36* | (2006.01) |
| *G01N 33/50* | (2006.01) |
| *C12N 5/00* | (2006.01) |
| *G01N 1/30* | (2006.01) |
| *B01D 21/00* | (2006.01) |

(52) U.S. Cl.
CPC .............. *G01N 1/36* (2013.01); *C12N 5/0081* (2013.01); *G01N 1/30* (2013.01); *G01N 33/50* (2013.01); *B01D 21/00* (2013.01); *C12N 5/00* (2013.01)

(58) Field of Classification Search
CPC ....................................................... G01N 1/36
See application file for complete search history.

(56) References Cited

FOREIGN PATENT DOCUMENTS

| | | |
|---|---|---|
| CN | 1699953 | 11/2005 |
| CN | 101957282 | 1/2011 |
| CN | 103116018 | 4/2015 |
| WO | 2009086487 | 7/2009 |

OTHER PUBLICATIONS

Nag et al. J. Anat. 1979, 129(3):541-559.*
Hedley et al. The J of Histochemistry and Cytochemistry, 1983, 31(11):1333-1335.*
Leers et al. Cytometry, 1997, 27:283-289.*
International Search Report dated Oct. 23, 2015 from application serial No. PCT/CN2015/077297.
Ren, Xingchang et al. "The Preparation and Preservation of Single Cell Suspension of Pathogenic" *Journal of Practical Medical Techniques*, vol. 14, 8, May 31, 2007, p. 971-972.
Tang, Guohua et al. "The Effect of Paraffin Section Thickness on Analysis of Flow Cytometer Cell Cycle Detection" *Journal of Nanjing University*, vol. I32, 2, Apr. 30, 2004.

* cited by examiner

*Primary Examiner* — Bin Shen
(74) *Attorney, Agent, or Firm* — Hogan Lovells US LLP

(57) ABSTRACT

Provided are a method for preparing a liquid-state dripping or coating pathological quality control product, and uses thereof. The method comprises: selecting and determining a control with a control value, and processing the control; adding an ethanol solution to the processed control for preserving for standby use, with the amount of the ethanol solution added depending on the amount of a precipitate; and performing setting of a positive or negative control by means of dripping or smearing. The pathological quality control product is a suspension or homogenate of micro tissue sections, cell/cultured cell sections, or cultured cells. Another aspect of the present invention provides a use of the liquid-state dripping or coating pathological quality control product as a positive or negative control in immunohistochemistry, in situ hybridization, special staining and other tissue staining detection, or as a standard quality control product for pathological internal quality control and external quality control.

10 Claims, 3 Drawing Sheets

METHOD FOR PREPARING LIQUID-STATE DRIPPING OR COATING PATHOLOGICAL QUALITY CONTROL PRODUCT AND USES THEREOF

This application is a U.S. National Phase application under 35 U.S.C. § 371 International Application PCT/CN2015/077297, filed on Apr. 23, 2015, which claims priority to Chinese application 201510062783.0, filed on Feb. 6, 2015, the contents of both which are incorporated by reference in their entirety.

BACKGROUND

The present invention relates to the technical field of biomedicine, and particularly to a method for preparing a liquid-state dripping or coating pathological quality control product by preparing a suspension or homogenate of a tissue- or cell-embedded section control whose antigen expression is exactly the same with that of an original tissue section, which achieves simple preparation, convenient and fast use and stable and reliable results, and to uses of the liquid-state dripping or coating pathological quality control product.

DETAILED DESCRIPTION

Figure 1:
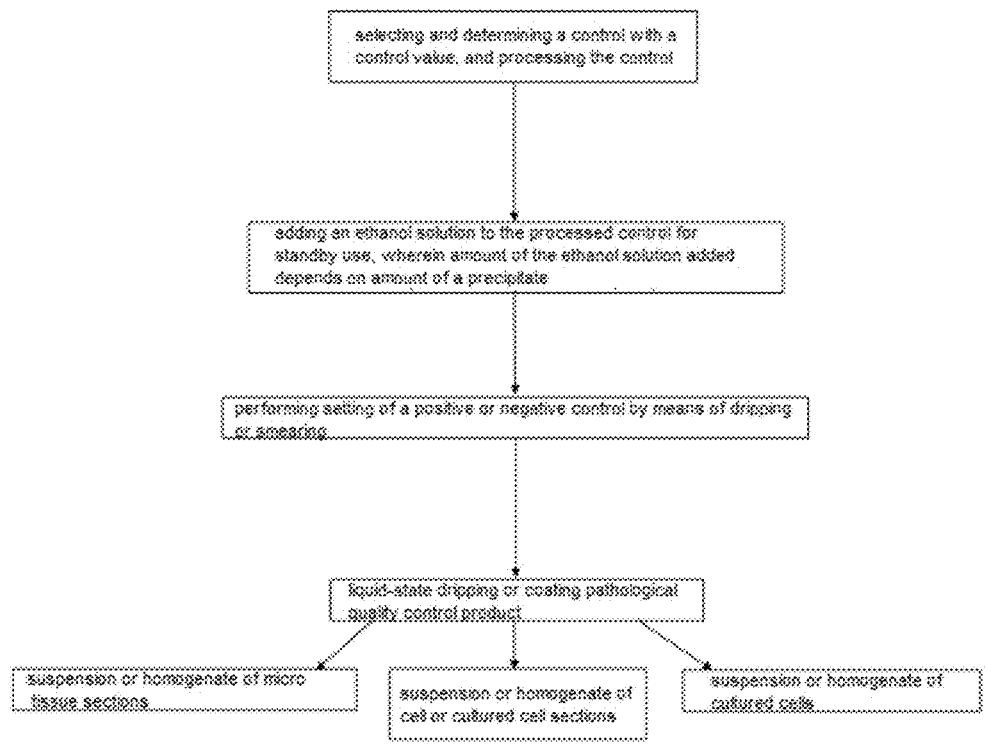
FIG. 1 shows a schematic flow block diagram of a process for preparing a liquid-state dripping or coating pathological quality control product provided by an example of the present invention.

Currently, in situ section staining technologies like immunohistochemistry, in situ hybridization and so on are widely used, but effective positive and negative controls must be established in practical work to ensure the accuracy of results based on which physicians can make correct diagnosis of diseases, and patients can get proper treatments. Currently, methods using gene chips or sausage-shaped paraffin sections, commonly used in the world, require that a control paraffin block is attached to a section to be examined after sectioned, which not only leads to heavy workload, long time to be consumed and complicated steps, but also results in a lot of tissue losses during each sectioning. Because of the above, they have not been well used in many laboratories. In addition, such sections are inclined to be oxidized in air, resulting in loss of antigens, so it is difficult to develop such control sections into commercial products.

In view of the above-mentioned problems existing in the prior art, an object of the present invention is to provide a method for preparing a liquid-state dripping or coating pathological quality control product by preparing a suspension or homogenate of a tissue- or cell-embedded section control whose antigen expression is exactly the same with that of an original tissue section, which achieves simple preparation, convenient and fast use and stable and reliable results, and uses of the liquid-state dripping or coating pathological quality control product.

In one aspect of the present invention, there is provided a method of preparing a liquid-state dripping or coating pathological quality control product, the method comprises the following steps:
 a) selecting and determining a control with a control value, and processing the control;
 b) adding an ethanol solution (preferably 75% ethanol solution) to the processed control for preserving for standby use, wherein the amount of the ethanol solution added depends on the amount of a precipitate; and
 c) performing setting of a positive or negative control by means of dripping or smearing.

Optionally, the pathological quality control product is a suspension or homogenate of micro tissue sections, a suspension or homogenate of cell or cultured cell sections, or a suspension or homogenate of cultured cells.

Preferably, the control contains a variety of antigenic information, and comprises tissue or cell sections.

Further, when the pathological quality control product is a suspension or homogenate of micro tissue sections, the step a) comprises the following steps:
 a) dewaxing the micro tissue sections, and performing immunohistochemistry, in situ hybridization and special staining detection according to a part where the micro tissue sections are from, morphology and tumor nature of the micro tissue sections, to determine antigen information and antigen intensity contained in the micro tissue sections, selecting the micro tissue sections with abundant positive cells and few interstitial cells and removing undesired tissues for standby use;
 b) sectioning step: performing continuous sectioning according to the tissue section thicknesses required for routine immunohistochemistry, in situ hybridization and special staining, and placing the obtained control sections in a container incapable of being dissolved by organic solvents, for standby use; and
 c) grinding the sections in the container into fine particles, adding dimethylbenzene to dissolve the sections completely, mixing and centrifuging, discarding dimethylbenzene, then adding absolute ethanol, mixing and centrifuging, and discarding absolute ethanol.

Optionally, when the pathological quality control product is a suspension or homogenate of micro cell sections, the step b) further comprises HE staining, wherein at least 100 cells are contained per microliter of the solution under a microscope, with an average cell debris size of 20~50 microns.

Further, when the pathological quality control product is a suspension or homogenate of cell sections, the step a) comprises the following steps:
 a) placing cells in neutral buffered formalin (preferably 10% neutral buffered formalin) for fixing for 1~4 h, centrifuging and discarding supernatant;

b) dehydrating the cells by alcohol whose concentration is gradually increased;
c) performing hyalinization, wax-dipping and embedding on the cells according to a conventional method;
d) sectioning step: performing continuous sectioning according to the tissue section thicknesses required for routine immunohistochemistry, in situ hybridization and special staining, and placing the obtained control sections in a container incapable of being dissolved by organic solvents, for standby use; and
e) adding dimethylbenzene to dissolve paraffin completely, mixing and centrifuging, discarding dimethylbenzene, then adding absolute ethanol, mixing and centrifuging, and discarding absolute ethanol.

Optionally, in the sectioning step, lymphoma sections have a thickness of 2~3 μm, and other tumor sections have a thickness of 3~5 μm.

Further, when the pathological quality control product is a suspension or homogenate of cultured cells, the step a) comprises the following steps: placing the cultured cells in neutral buffered formalin (preferably 10% neutral buffered formalin) for fixing for 1~4 h, centrifuging, and discarding supernatant.

Optionally, when the pathological quality control product is a suspension or homogenate of cell sections or suspension or homogenate of cultured cells, the step b) further comprises HE staining, wherein at least 50 cells are contained per microliter of the solution under a microscope.

In another aspect of the present invention, there is provided a use of the liquid-state dripping or coating pathological quality control product, prepared according to the method provided by the present invention, as a positive or negative control in immunohistochemistry, in situ hybridization, special staining and other tissue staining detection processes (to verify the accuracy of a sample detection), or a use of the liquid-state dripping or coating pathological quality product, prepared according to the method provided by the present invention, as a standard quality control product for pathological internal quality control and external quality control.

By adopting the above technology, compared to the prior art, the method of preparing a liquid-state dripping or coating pathological quality control product and the application thereof provided by the present invention provide one of the following beneficial effects:

1. In the method of preparing a liquid-state dripping or coating pathological quality control product provided by present invention, paraffin-embedded sections are used, so that the control cells or tissue particles will have morphology, thickness and positive expression exactly the same with those of sample sections to be detected, thereby ensuring the accuracy of the pathological detection results. In addition, the controls prepared by the method have certain organization levels and structures, which are more visible and reliable for observers.

2. The ethanol solution, used as the solution for preserving the control, not only may be evaporated and dried immediately after dripped or smeared, without the inclination of falling off from the sections and with uniform cell distribution, but also may preserve antigens for a long time.

3. It is widely used, as it can verify the accuracy of results of various laboratories and the correctness of detection by reagents and detection systems provided by various manufacturers, may also be used as an index of quality control in immunohistochemistry, in situ hybridization and special staining, and further, may be used as the standard quality control product for pathological internal quality control and external quality control.

4. The positive or negative control is set by means of dripping or smearing, reducing a lot of workload, greatly shortening operating time, and thus being time and effort effective.

5. The positive control and negative controls may be mixed in proportion, so that the loading of the positive and negative controls may be done at a time.

6. The cells (including cultured cells) are prepared into a suspension or homogenate after being fixed, dehydrated, embedded and sectioned, enabling mass production and preparation and usage in batches in the industry of positive or negative control sections, and thus achieving commercialization.

Exemplary examples of the present invention will now be described in detail with reference to the accompanying drawings. These exemplary examples are provided so that those skilled in the art will be able to clearly understand the present invention and implement the present invention according to the description herein. The drawings and the specific examples are not intended to limit the present invention. The scope of the present invention is defined by the appended claims.

Figure 2:
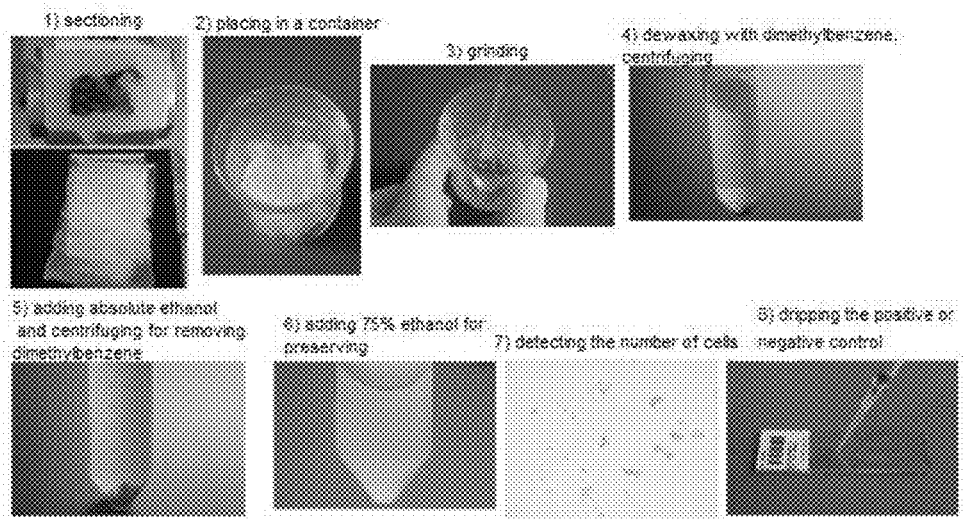
FIG. 2 shows a schematic diagram showing partial process for preparing a liquid-state dripping or coating pathological quality control product provided by an example of the present invention (a suspension or homogenate of micro tissue sections being used as control)

FIG. 1 shows a schematic block diagram of a process for preparing a liquid-state dripping or coating pathological quality control product provided by an example of the present invention; FIG. 2 shows a schematic diagram showing partial process for preparing a liquid-state dripping or coating pathological quality control product provided by an example of the present invention (a suspension or homogenate of micro tissue sections being used as control). Referring to FIGS. 1 and 2, when the pathological quality control product is a suspension or homogenate of micro tissue sections, the method of preparing a liquid-state dripping or coating pathological quality control product comprises the following steps:

1) dewaxing the micro tissue sections (i.e. original paraffin sections) and performing immunohistochemistry, in situ hybridization and special staining detection according to a part where the micro tissue sections are from, morphology and the tumor nature of the micro tissue sections, to determine antigen (or protein) information and antigen intensity, contained in the micro tissue sections, selecting the micro tissue sections (or paraffin blocks) with abundant positive cells and few interstitial cells as much as possible, and removing undesired tissues for standby use;

2) sectioning step: performing continuous sectioning according to the tissue section thicknesses required for routine immunohistochemistry, in situ hybridization and special staining (a thickness of 2~3 μm for lymphoma sections, and a thickness of 3~5 μm for other tumor sections), and placing the obtained control sections in a container (the container was preferably a centrifuge tube) incapable of being dissolved by organic solvents, for standby use;

3) grinding the sections in the container into fine particles, adding dimethylbenzene to dissolve the paraffin sections completely, mixing for 5 minutes with a swift mixer (to reduce tissue debris or overlapped cells, and hereinafter, all mixing by using the swift mixer is for this purpose), centrifuging (3,000 rpm, 2 minutes), discarding dimethylbenzene, then adding absolute ethanol, mixing for 5 minutes with the swift mixer, centrifuging (3,000 rpm, 2 minutes), and discarding absolute ethanol;

4) adding an ethanol solution (preferably 75% ethanol solution) to the processed control for preserving for standby use, wherein the amount of the ethanol solution added depended on the amount of a precipitate (HE staining, wherein at least 100 cells were contained per microliter of the solution under a microscope, that is, ≥100 cells were contained per microliter of the solution under a microscope, with an average cell debris size of 20~50 microns, preferably 30~40 microns), and mixing them for 5 minutes with the swift mixer; and 5) performing setting of a positive or negative control by means of dripping or smearing, and dripping or smearing the control beside a sample to be detected.

When the pathological quality control product is a suspension or homogenate of cell or cultured cell sections, the method of preparing a liquid-state dripping or coating pathological quality control product comprises the following steps:

1) placing the cells or cultured cells in 10% neutral buffered formalin for fixing for 1~4 h, centrifuging (3,000 rpm, 2 minutes), and discarding supernatant;

2) dehydrating the cells by alcohol whose concentration is gradually increased, that is, adding 75% ethanol, centrifuging 30~60 minutes later (3,000 rpm, 2 minutes), and discarding supernatant; adding 95% ethanol, centrifuging 30~60 minutes later (3,000 rpm, 2 minutes), and discarding supernatant; and adding absolute ethanol, centrifuging 30~60 minutes later (3,000 rpm, 2 minutes), and discarding supernatant;

3) performing hyalinization, wax-dipping and embedding on the cells according to a conventional method, that is, adding dimethylbenzene, centrifuging 15 minutes later (3,000 rpm, 2 minutes), and discarding supernatant; adding 1~2 mL of melted paraffin, placing in an incubator at 60° C. for 30~60 minutes, centrifuging immediately after taking them out (3,000 rpm, 2 minutes); placing in a freezing chamber of a refrigerator for cooling for 30 minutes, then taking the solidified paraffin (tissues or cells) out for embedding;

4) sectioning step: performing continuous sectioning according to the tissue section thicknesses required for routine immunohistochemistry, in situ hybridization and special staining (a thickness of 2~3 μm for lymphoma sections, and a thickness of 3~5 μm for other tumor sections), and placing the obtained control sections in a container (the container was preferably a centrifuge tube) incapable of being dissolved by organic solvents, for standby use;

5) adding dimethylbenzene to dissolve the paraffin completely, mixing for 5 minutes with a swift mixer, centrifuging (3,000 rpm, 2 minutes), discarding dimethylbenzene, then adding absolute ethanol, mixing for 5 minutes with the swift mixer, centrifuging (3,000 rpm, 2 minutes), and discarding absolute ethanol;

6) adding an ethanol solution (preferably 75% ethanol solution) to the processed control for preserving them for standby use, wherein the amount of the ethanol solution added depended on the amount of a precipitate (HE staining, wherein at least 50 cells were contained per microliter of the solution under a microscope, that is, ≥50 cells were contained per microliter of the solution under a microscope), and mixing for 5 minutes with the swift mixer; and 7) performing setting of a positive or negative control by means of dripping or smearing, and dripping or smearing the controls beside a sample to be detected.

When the pathological quality control product is a suspension or homogenate of cultured cells, the method of preparing a liquid-state dripping or coating pathological quality control product comprises the following steps:

1) placing the cultured cells in 10% neutral buffered formalin for fixing for 1~4 h, centrifuging (3,000 rpm, 2 minutes), and discarding the supernatant;

2) adding an ethanol solution (preferably 75% ethanol solution) to the processed control for preserving for standby use, wherein the amount of the ethanol solution added being depended on the amount of a precipitate (HE staining, wherein at least 50 cells were contained per microliter of the solution under a microscope, that is, ≥50 cells were contained per microliter of the solution under a microscope), and mixing for 5 minutes with a swift mixer; and 3) performing setting of a positive or negative control by means of dripping or smearing.

It should be noted that, in the method of preparing a liquid-state dripping or coating pathological quality product provided by the present invention, the ethanol solution (preferably 75% ethanol solution) was added to the processed control for preserving for standby use, wherein the concentration of the ethanol solution may be determined according to the actual condition of a user or experimental requirements, and is not limited to a certain concentration of ethanol solution, but 75% ethanol solution is preferable; in the method of preparing a liquid-state dripping or coating pathological quality control product provided by the present invention, when the pathological quality control product is a suspension or homogenate of cell or cultured cell sections, or a suspension or homogenate of cultured cells, neutral buffered formalin is used for fixing, wherein the concentration of the neutral buffered formalin also is not limited to a certain concentration of a neutral buffered formalin, but 10% neutral buffered formalin is preferable, for example, it may be 12%~15% neutral buffered formalin.

Figure 3:
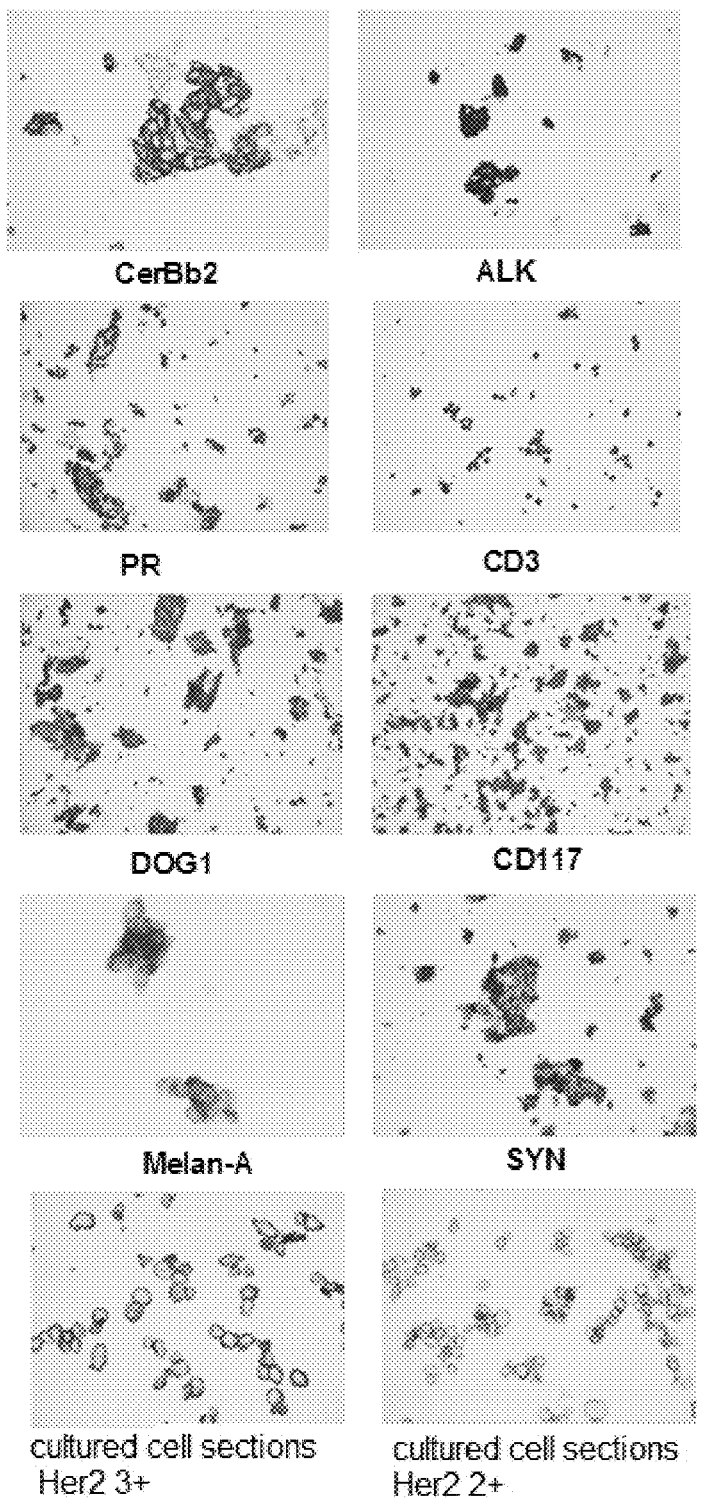
FIG. 3 shows an immunohistochemical profile of a liquid-state dripping or coating pathological quality control product provided by multiple examples of the present invention as a positive sample tissue section to be detected (pictures under a Leica DM 2500 microscope, 40×)
Figure 4:
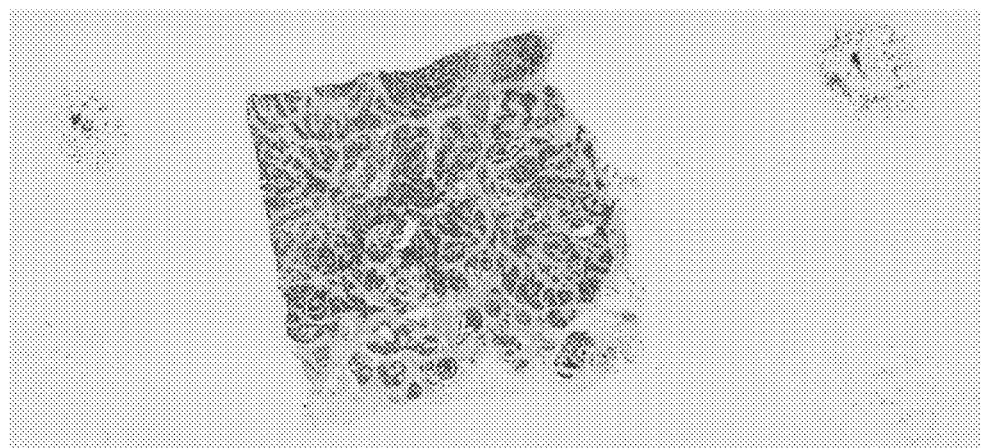
FIG. 4 shows an appearance picture, scanned by an Aperio scanner, of a liquid-state dripping or coating pathological quality control product, prepared according to a method of preparing a liquid-state dripping or coating pathological quality control product provided by an example of the present invention, as a final section positive control for sample loading.

FIG. 3 shows an immunohistochemical profile of a liquid-state dripping or coating pathological quality control product provided by multiple examples of the present invention as a positive sample tissue section to be detected (pictures under a Leica DM 2500 microscope, 40×), wherein cells, which become brown after histological staining, were tumor cells as shown in the figure. FIG. 4 shows an appearance picture, scanned by an Aperio scanner, of a liquid-state dripping or coating pathological quality control product, prepared according to a method of preparing a liquid-state dripping or coating pathological quality control product provided by an example of the present invention, as a final section positive control for sample loading. Referring to FIGS. 3 and 4, a use of the pathological quality control product as a suspension or homogenate of micro tissue sections, a suspension or homogenate of cell sections or a suspension or homogenate of cultured cells was implemented by a method comprising: first observing for the control whether results were correct, whether location was correct and whether positive intensity was proper, when performing interpretation on samples subjected to immunohistochemistry, in situ hybridization, special staining and the like, that is:

1) if the control showed correct results, the sample sections to be detected should be observed to determine whether the results were positive or negative.

2) if the control did not express correct results, the cause should be found, and re-detection should be done.

The foregoing description is merely directed to preferable examples of the present invention, rather than limiting the present invention. And various modifications and variations may be made to the present invention by those skilled in the art. Any modifications, equivalent substitutions, improvements and the like, made within the spirit and principle of the present invention, are intended to be included within the scope of the present invention.

What is claimed is:

1. A method for preparing a control sample of a suspension or homogenate of cells or a cultured cell section wherein the control sample has the same antigen expression of the cells or the cultured cell section as an original tissue section, the method comprising:
   a) placing the suspension or homogenate of cells or cultured cell section in a neutral buffered formalin for fixing for 1 to 4 hours, centrifuging, and discarding supernatant to obtain formalin processed cells;
   b) dehydrating the formalin processed cells from step a) with an alcohol 3-step process wherein the 3-step process comprises:
      i) mixing the formalin processed cell with a 75% ethanol solution, centrifuging and removing supernatant;
      ii) mixing with a 95% ethanol solution, centrifuging and removing supernatant; and
      iii) mixing with an absolute ethanol solution, centrifuging and removing supernatant to obtain a dehydrated cell sample;
   c) embedding the dehydrated cell sample by performing hyalinization, wax-dipping and embedding of the cells to obtain a paraffin embedded cell sample;
   d) obtaining a section of the paraffin embedded cell sample;
   e) adding dimethylbenzene to the paraffin embedded cell sample to dissolve the paraffin, mixing and centrifuging, removing the dimethylbenzene, adding absolute ethanol, mixing and centrifuging, and discarding the absolute ethanol to obtain a control sample;
   f) adding a 75% ethanol solution, and completely oscillating and mixing, wherein the amount of ethanol is at least 100 cells contained per microliter; and
   g) applying the control sample to a glass slide by manual dripping or machine-automatic dripping the control sample onto the glass slide; and
   wherein the control sample has the same antigen expression as the original tissue section.

2. The preparation method according to claim 1, wherein when the pathological quality control product is the suspension or homogenate of micro tissue sections, the step a) comprises following steps:
   dewaxing the micro tissue sections and performing immunohistochemistry, in situ hybridization and special staining detection according to a part where the micro tissue sections are from, morphology and tumor nature of the micro tissue sections, to determine antigen information and antigen intensity contained in the micro tissue sections, selecting the micro tissue sections with abundant positive cells and few interstitial cells and removing undesired tissues for standby use;
   performing continuous sectioning according to a tissue section thicknesses required for routine immunohistochemistry, in situ hybridization and special staining, and placing the obtained control sections in a container incapable of being dissolved by organic solvents, for standby use;
   grinding the sections in the container into fine particles, adding dimethylbenzene to dissolve the sections completely, mixing and centrifuging, discarding dimethylbenzene, then adding absolute ethanol, mixing and centrifuging, and discarding absolute ethanol.

3. The preparation method according to claim 2, wherein the step b) further comprises HE (hematoxylin and eosin) staining, and at least 100 cells are contained per microliter of the solution under a microscope, with an average cell debris size of 20~50 microns.

4. The preparation method according to claim 2, wherein in the sectioning step, lymphoma sections have a thickness of 2~3 μm, and other tumor sections have a thickness of 3~5 μm.

5. The preparation method according to claim 1, wherein when the pathological quality control product is the suspension or homogenate of cultured cells, the step a) comprises following steps: placing the cultured cells in neutral buffered formalin for fixing for 1~4 h, centrifuging, and discarding supernatant.

6. The preparation method according to claim 5, wherein the step b) further comprises HE staining, and at least 50 cells are contained per microliter of the solution under a microscope.

7. The method according to claim 1, further comprising staining the control sample.

8. The method of claim 1 wherein the neutral buffered formalin is a 12 to 15% neutral buffered formalin.

9. The method of claim 1 wherein the neutral buffered formalin is a 10% neutral buffered formalin.

10. The method according to claim 1, wherein step d) comprises the step of:
    performing continuous sectioning according to a tissue section thicknesses required for routine immunohistochemistry; in situ hybridization and special staining to obtain a section of the paraffin embedded cell sample.

* * * * *